(12) United States Patent
Ikeda et al.

(10) Patent No.: US 8,138,122 B2
(45) Date of Patent: Mar. 20, 2012

(54) HERBICIDAL COMPOSITION

(75) Inventors: Hajime Ikeda, Kobe (JP); Satoru Kizawa, Kakogawa (JP)

(73) Assignee: Sumitomo Chemical Company, Limited, Tokyo (JP)

( * ) Notice: Subject to any disclaimer, the term of this patent is extended or adjusted under 35 U.S.C. 154(b) by 403 days.

(21) Appl. No.: 12/298,499

(22) PCT Filed: Apr. 12, 2007

(86) PCT No.: PCT/JP2007/058474
§ 371 (c)(1),
(2), (4) Date: Jan. 27, 2009

(87) PCT Pub. No.: WO2007/125808
PCT Pub. Date: Nov. 8, 2007

(65) Prior Publication Data
US 2009/0186763 A1 Jul. 23, 2009

(30) Foreign Application Priority Data
Apr. 28, 2006 (JP) .................. 2006-125005

(51) Int. Cl.
*A01N 43/58* (2006.01)
*A01N 43/60* (2006.01)
*A01N 63/00* (2006.01)

(52) U.S. Cl. ................. 504/137; 504/118; 504/136

(58) Field of Classification Search .................. 504/137, 504/136
See application file for complete search history.

(56) References Cited

U.S. PATENT DOCUMENTS 5,017,212 A 5/1991 Ishida et al.
6,486,096 B1 11/2002 Hacker et al.

2003/0191025 A1 10/2003 Hacker et al.
2005/0032650 A1 2/2005 Tanaka et al.
2005/0250647 A1 11/2005 Hills et al.

FOREIGN PATENT DOCUMENTS

| AU | 85572/91 B | 4/1992 |
| DE | 4241629 A1 | 6/1994 |
| EP | 1466527 A1 | 10/2004 |
| JP | 2005-126415 A | 5/2005 |

OTHER PUBLICATIONS

Opinion on the Evaluation of Imazosulfuron [TH-913] in the Context of Council Directive 91/414/EEC Concerning the Placing of Plant Protection Products on the Market, May 2001, Scientific Committee on Plants, European Commission Health and Consumer Protection Directorate-General, 15 pages.*

* cited by examiner

*Primary Examiner* — Johann Richter
*Assistant Examiner* — Andriae M Holt
(74) *Attorney, Agent, or Firm* — Birch, Stewart, Kolasch & Birch, LLP

(57) ABSTRACT

A herbicidal composition which comprises 1-(2-chloroimidazo[1,2-a]pyridin-3-ylsulfonyl)-3-(4,6-dimethoxypyrimidin-2-yl)urea (imazosulfuron) and a compound represented by the formula (I):

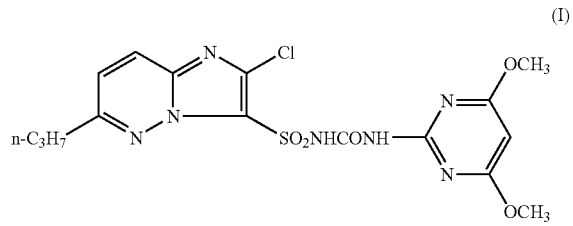

(Compound [I]) as active ingredients, wherein the weight ratio of imazosulfuron: Compound [I] is 1:0.1-1:10, has an excellent herbicidal activity for controlling weeds in crop fields or paddy fields, and causes no phytotoxicity against useful plants.

4 Claims, No Drawings

HERBICIDAL COMPOSITION

TECHNICAL FIELD

This invention directs to a herbicidal composition and a herbicidal method.

BACKGROUND ART

At the present time, numerous herbicides are commercially available and they are widely used. There are, however, a wide variety of weeds to be controlled and their growth extends over a long time. For this reason, requested are herbicides with higher herbicidal activity, a wide weed control spectrum, long term effect, and safety to crops.

DISCLOSURE OF THE INVENTION

This invention provides a composition and a method for controlling a wide variety of weeds by higher herbicidal effect without phytotoxicity to crops.

Namely, the invention provides a herbicidal composition which comprises 1-(2-chloroimidazo[1,2-a]pyridin-3-ylsulfonyl)-3-(4,6-dimethoxypyrimidin-2-yl)urea (imazosulfuron) and a compound represented by the formula (I):

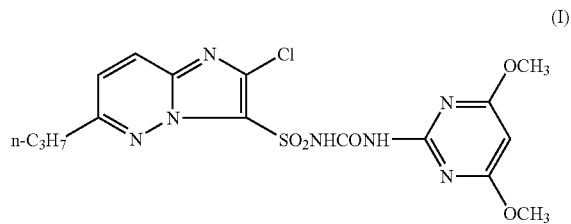

(Compound [I]) as active ingredients, wherein the weight ratio of imazosulfuron: Compound [I] is 1:0.1-1:10.

Further, it provides a herbicidal method which comprises applying imazosulfuron and Compound [I] to weeds or soil in a place where the weeds grow or will grow, wherein the weight ratio of imazosulfuron: Compound [I] is 1:0.1-1:10.

Imazosulfuron [Chemical name: 1-(2-chloroimidazo[1,2-a]pyridin-3-ylsulfonyl)-3-(4,6-dimethoxypyrimidin-2-yl)urea, CAS RN 122548-33-8], which is a compound given by the formula:

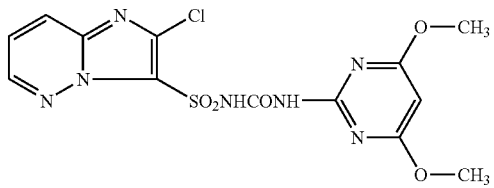

is a herbicidally active compound described in U.S. Pat. No. 5,017,212. It can be prepared by a known production method, and the formulations containing imazosulfuron are available on the market.

Compound [I] can be prepared by a known production method described in USP 2005-0032650A.

The herbicidal composition of the present invention comprises imazosulfuron and Compound [I] as active ingredients and the ratio of imazosulfuron: Compound [I] in the herbicidal composition is 1:0.1-1:10, preferably 1:0.5-1:2 by weight.

The herbicidal composition has herbicidal activity against a variety of weeds, and thus, can be used for controlling a wide variety of weeds effectively in the fields, where crops are cultivated with or without tillage or in a paddy field. Further, it does not cause significant phytotoxicity to useful plants.

The present invention also provides a method for controlling weeds which comprises applying jointly or simultaneously imazosulfuron and Compound [I] to weeds or soil in a place where the weeds grow or will grow, wherein the ratio of imazosulfuron: Compound [I] is 1:0.1-1:10, preferably 1:0.5-1:2 by weight.

The method can be used for controlling weeds, especially in crop fields or paddy fields.

Examples of the crop field in the present invention include the fields of edible crops such as peanut, soybean, corn, wheat, barley and rye; feed crops such as sorghum and oat; industrial crops such as cotton; sugar crops such as sugarcane; and vegetables such as Solanaceae vegetables (e.g., eggplant, tomato, green pepper, red pepper and potato), Cucurbitaceae vegetables (e.g., cucumber, pumpkin, zucchini, watermelon and melon), Brassicaceae vegetables (e.g., radish, turnip, horseradish, cohlrabi, Chinese cabbage, cabbage, leaf mustard, broccoli and cauliflower), Compositae vegetables (e.g., burdock, crown daisy, artichoke and lettuce), Liliaceae vegetables (e.g., leek, onion, garlic and asparagus), Umbelliferae vegetables (e.g., carrot, parsley, celery and parsnip), Chenopodiaceae vegetables (e.g., spinach and chard), Lamiacea vegetables (e.g., perilla, mint, basil and lavender), strawberry, sweet potato, yam and taro.

The paddy field is a heavily irrigated or lightly flooded piece of land in which rice is grown.

Examples of the weeds include annual weeds and perennial weeds which grow in crop field or paddy field. Typical examples include *Echinochloa oryzicola* (barnyardgrass, watergrass), *Echinochloa crus-galli* (barnyardgrass), *Scirpus juncoides* (bulrush), *Scirpus mucronatus* (rice-field bulrush), *Scirpus planiculmis, Scirpus nipponicus, Cyperus difformis* (smallflower umbrella plant), *Cyperus serotinus* (water nutgrass), *Eleocharis kuroguwai* (water chestnut), *Monochoria vaginalis, Sagittaria pygmaea* (dwarf arrowhead), *Sagittaria trifolia, Lindernia pocumbens* (common falsepimpernel), *Lindernia dubia* (low falsepimpernel), *Lindernia angustifolia, Gratiola japonica, Rotala indica* (Indian toothcup), *Elatine triandra* (waterwort), *Alisma canaliculatum* (waterplantain), *Ammannia coccinea* (purple redstem), *Bidens tripartita* (bur beggarticks), *Bidens frondosa* (devils beggarticks), *Aeschynomene indica* (indian jointvetch), *Seshania exaltata* (hemp sesbania), *Oenanthe javanica, Potamogeton distinctus* (roundleaf pondweed), *Galium aparine* (cleavers), *Galium spurium* (false cleavers), *Sinapis arvensis* (wild mustard), *Brassica juncea* (Indian mustard), *Stellaria media* (common chickweed), *Matricaria chamomilla* (wild chamomile), *Ipomoea* spp. (morningglories), *Amaranthus* spp., *Polygonum* spp., *Abutilon theophrasti* (velvetleaf), *Xanthium strumarium* (common cocklebur), *Ambrosia artemisiifolia* (common ragweed), *Taraxacum officinale* (dandelion), *Cyperus rotundus* (purple nutsedge) and *Cyperus esculentus* (yellow nutsedge). The herbicidal composition of the present invention is effective for controlling these weeds and it does not cause significant phytotoxicity to useful plants, especially rice, wheat, barley, rye and oat.

The herbicidal composition can be formulated to emulsifiable concentrates, oil solution, spray formulation, wettable powders, dusts, DL dusts (driftless type), granules, fine granules, fine granules F, flowables, dry flowables, jumbo formulations, tablets and so on by dissolving or dispersing the active ingredients in a liquid carrier, or mixing with a solid carrier. These formulations can be obtained by conventional methods and may further contain emulsifiers, dispersants, adjuvants, penetrating agents, wetting agents, sticking agents, stabilizers and so on. These formulations generally contain about 0.01 to 90% by weight of the total amount of imazosulfuron and Compound [I]. Emulsifiable concentrates, wettable powders, spray formulation, dry flowables or flowables generally contain about 1 to 90% by weight; oil solution, dusts or DL dusts generally contain about 0.01 to 10% by weight; and fine granules, fine granules F, jumbo formulations, granules or tablets generally contain about 0.05 to 10% by weight.

Examples of the liquid carrier include water; alcohols such as methanol, ethanol, 1-propanol, 2-propanol and ethylene glycol; ketones such as acetone and methyl ethyl ketone; ethers such as dioxane, tetrahydrofuran, ethylene glycol monomethyl ether, diethylene glycol monomethyl ether and propylene glycol monomethyl ether; aliphatic hydrocarbons such as kerosene, fuel oil and machine oil; aromatic hydrocarbons such as benzene, toluene, xylene, solvent naphtha and methylnaphthalene; halogenated hydrocarbons such as dichloromethane, chloroform and carbon tetrachloride; acid amides such as dimethylformamide and dimethylacetamide; esters such as ethyl acetate, butyl acetate and glycerin esters of fatty acids; and nitriles such as acetonitrile and propionitrile. A mixture of two or more liquid carriers may be used as well as a sole liquid carrier. Examples of the solid carrier include plant powders such as soybean powder, tobacco powder, wheat powder and wood powder; mineral powders such as kaolinite, bentonite, terra alba, clay, talc, pyrophyllite powder, diatomaceous earth, mica powder and silica; almina; sulfur powder; and activated carbon. A mixture of two or more solid carriers may be used as well as a sole solid carrier. The formulations generally contain about 1 to 99% by weight, preferably about 1 to 80% by weight of the total amount of the liquid carrier and the solid carrier.

Examples of the surfactant used for the emulsifier, dispersant, adjuvant or penetrating agent include nonionic surfactants and anionic surfactants. Typical examples are soaps, polyoxyethylene alkylaryl ethers (e.g., Noigen and EA142 produced by Dai-ichi Kogyo Seiyaku Co., Ltd.), polyoxyethylene ary esters (e.g., Nonal produced by Toho Chemical), alkyl sulfate salts (e.g., Emal 10 and Emal 40 produced by Kao Corp.), alkylbenzenesulfonate (e.g., Neogen and Neogen T produced by Dai-ichi Kogyo Seiyaku, Neopelex produced by Kao Corp.), polyethylene glycol ethers (e.g., Nonipol 85, Nonipol 100 and Nonipol 160 produced by Sanyo Chemical Industries, Ltd.) and polyvalent alcohol esters (e.g., Tween 20 and Tween 80 produced by Kao Corp.). The formulations generally contain about 0.1 to 50% by weight, preferably about 0.1 to 25% by weight of the surfactant.

The herbicidal composition can also be prepared by mixing each formulation after formulating each of the active ingredients with conventional procedure.

The herbicidal composition can be applied as it is for the herbicidal method of the present invention. Further, it can be diluted with water or the like, and then the dilution can be applied to soil or a plant. Emulsifiable concentrates, wettable powders and dry flowables are generally diluted with water and the like to an appropriate volume (e.g., 100 to 100,000-fold dilution), and then applied. It may be expected to increase the herbicidal effect by using the herbicidal composition of the invention together with another herbicide. Moreover, the herbicidal composition can be used with insecticides, fungicides, plant growth regulators, fertilizers, safeners, soil-improving agents and so on.

When the herbicidal composition is used in a paddy field, it can be applied after seeding in the flooded field, after seeding in the dry field, at the time of the transplant or after the transplant of rice. When the herbicidal composition is used in a crop field, especially a wheat field or a barley field, it is applied by soil treatment before germination or by both foliar and soil treatment. The herbicidal composition does not cause phytotoxicity, and thus it is safe for crops.

The dosage of the herbicidal composition or method depends on the mixing ratio of imazosulfuron and Compound [I] as active ingredients, weather condition, formulation types, application time, application methods, application places, objective weeds and crops, and it is usually about 30 to 400 g, preferably 50 to 200 g of the total amount of the active ingredients per hectare in a paddy field. It is usually about 30 to 2000 g, preferably 50 to 1000 g of the total amount of the active ingredients per hectare in a crop field.

EXAMPLES

Hereinafter, the present invention is explained by examples in detail.

Formulation examples are given below. In the following examples, part(s) means part(s) by weight.

Formulation Example 1

One (1.0) part of imazosulfuron, 1.0 part of Compound [I], 0.5 part of Neocol YSK (sodium dialkylsulfosuccinate ester produced by Dai-ichi Kogyo Seiyaku Co., Ltd.), 2.0 parts of Toxanon GR31A (polycarboxylic acid type anionic surfactant produced by Sanyo Chemical Industries, Ltd.), 30 parts of Kunigel V1 (bentonite produced by Kuminine Industries Co., Ltd.) and 65.5 parts of calcium carbonate are charged into a small kneader, mixed, kneaded, granulated by extruder (RG-5M produced by Kikusui Seisakusho, Ltd.) and dried by fluidized bed dryer (MDB-400 produced by Fuji-Paudal Co., Ltd.), and then filtered with 16-48 mesh to give granules.

Formulation Example 2

Nineteen tenth (1.9) parts of imazosulfuron, 1.9 part of Compound [I], 9.0 parts of ethylene glycol, 0.3 parts of Antifoam E-20 (antifoaming agent produced by Kao Corp.), 0.1 part of sorbic acid, 10.0 parts of Isoelite L (cyclodextrin produced by Ensuiko Sugar Refining Co., Ltd.), 3.0 parts of New Kalgen D-1518, 2.0 parts of Agrisol FL-2017 (anionic/nonionic surfactant produced by Kao Corp.) and 71.8 parts of water are mixed and dispersed by homomixer, and then the mixture is wet-pulverized (one pass) by Dyno-Mill (produced by Shinmaru Enterprises Corp., 11.0 mm of glass beads, 85% of packing ratio, 10 m/s of rotating speed) to give flowable.

Formulation Example 3

Twenty-four tenth (2.4) parts of imazosulfuron, 2.4 part of Compound [I], 2.4 parts of Microsphere F-80E (hollow plastic produced by Matsumoto Yushi-Seiyaku Co., Ltd.), 3.0 parts of Olfine E1010 (polyoxyethylene acetylenediol produced by Nissin Chemical Industry Co., Ltd.), 2.0 parts of Toxanon GR31A (polycarboxylic acid type anionic surfactant produced by Sanyo Chemical Industries, Ltd.), 5.0 parts of sodium tripolyphosphate, 3.0 parts of Cellogen 7A (sodium carboxymethylcellulose produced by Dai-ichi Kogyo Seiyaku Co., Ltd.), 10.0 parts of Kunigel V1 (bentonite produced by Kuminine Industries Co., Ltd.) and 69.8 parts of calcium carbonate are mixed, kneaded with a suitable amount of water granulated by extruder (RG-5M produced by Kikusui Seisakusho, Ltd.) with 1.5 mm screen and dried by fluidized bed dryer (MDB-400 produced by Fuji-Paudal Co., Ltd.) to give granules.

Test Example 1

Foamed styrene pots each having an opening area of 50 $cm^2$ were filled with paddy field soil, flooded, and then seeded with watergrass (*Echinochloa oryzicola*). Each of imazosulfuron and Compound [I] was dissolved in acetone containing 2% (w/v) of Tween 20 (surfactant, sorbitan monolaurate polyglycol ether, trademark of ICI Americas), and then diluted with water to make the concentration of acetone to 10%. The prepared dilutions in the designated amount in Table 1 were applied to the pots when the watergrass reached 2.5- to 3-leaf stage. The pots were kept flooded 5 cm in depth after the application.

The herbicidal effect against the watergrass was examined 3 weeks after the application. The results are shown in Table 1.

TABLE 1

| Application dosage (g/ha) | | |
|---|---|---|
| imazosulfuron | Compound [I] | Herbicidal effect (%) |
| 45 | 45 | 85 |

Test Example 2

Foamed styrene pots each having an opening area of 50 cm² were filled with paddy field soil, flooded, and then seeded with *monochoria* (*Monochoria vaginalis*). Each of imazosulfuron and Compound [I] was dissolved in acetone containing 2% (w/v) of Tween 20 (surfactant), and then diluted with water to make the concentration of acetone to 10%. The prepared dilutions in the designated amount in Table 2 were applied to the pots when the *monochoria* reached 2.5- to 3-leaf stage. The pots were kept flooded 5 cm in depth after the application.

The herbicidal effect against the *monochoria* was examined 3 weeks after the application. The results are shown in Table 2.

TABLE 2

| Amount of active ingredient (g/ha) | | |
|---|---|---|
| imazosulfuron | Compound [I] | Herbicidal effect (%) |
| 45 | 45 | 86 |

Test Example 3

Plastic pots (590 cm²×28 cm) were filled with steam-sterilized soil, seeded with cleavers (*Galium aparine*), and the covered with 1 cm of soil. Imazosulfuron suspension was prepared by diluting Sibatito 40 (suspensible concentrate containing 40% of imazosulfuron produced by Sumitomo Chemical Takeda Agro Company) with water. Compound [I] dilution was prepared by dissolving Compound [I] in acetone containing 2% (w/v) of Tween 20 (surfactant), and then diluting with water to make the concentration of acetone to 10%. Further, the imazosulfuron suspension and Compound [I] dilution prepared above were mixed in the designated ratio in Table 3 to prepare the mixture containing imazosulfuron and Compound [I]. On the surface of the soil of the pots, each preparation was applied in the designated amount given in Table 3.

The herbicidal effect against the cleavers was examined 3 weeks after the application. The results are shown in Table 3.

TABLE 3

| Test compound | Amount of active ingredient (g/ha) | Herbicidal effect (%) |
|---|---|---|
| imazosulfuron | 100 | 10 |
| Compound [I] | 50 | 0 |
|  | 100 | 50 |
| imazosulfuron + Compound [I] | 100 + 50 | 40 |
|  | 100 + 100 | 80 |

Test Example 4

Plastic pots (590 cm²×28 cm) were filled with steam-sterilized soil, seeded with wild mustard (*Sinapis arvensis*), and the covered with 1 cm of soil. Imazosulfuron suspension was prepared by diluting Sibatito 40 (suspensible concentrate containing 40% of imazosulfuron produced by Sumitomo Chemical Takeda Agro Company) with water. Compound [I] dilution was prepared by dissolving Compound [I] in acetone containing 2% (w/v) of Tween 20 (surfactant), and then diluting with water to make the concentration of acetone to 10%. Further, the imazosulfuron suspension and Compound [I] dilution prepared above were mixed in the designated ratio in Table 4 to prepare the mixture containing imazosulfuron and Compound [I]. On the surface of the soil of the pots, each preparation was applied in the designated amount given in Table 4.

The herbicidal effect against the wild mustard was examined 3 weeks after the application. The results are shown in Table 4.

TABLE 4

| Test compound | Amount of active ingredient (g/ha) | Herbicidal effect (%) |
|---|---|---|
| imazosulfuron | 50 | 10 |
| Compound [I] | 25 | 10 |
| imazosulfuron + Compound [I] | 50 + 25 | 80 |

Test Example 5

Plastic pots (590 cm²×28 cm) were filled with steam-sterilized soil, seeded with wheat and the covered with 1 cm of soil. Imazosulfuron suspension was prepared by diluting Sibatito 40 (suspensible concentrate containing 40% of imazosulfuron produced by Sumitomo Chemical Takeda Agro Company) with water. Compound [I] dilution was prepared by dissolving Compound [I] in acetone containing 2% (w/v) of Tween 20 (surfactant), and then diluting with water to make the concentration of acetone to 10%. Further, the imazosulfuron suspension and Compound [I] dilution prepared above were mixed in the designated ratio in Table 6 to prepare the mixtures containing imazosulfuron and Compound [I]. On the surface of the soil of the pots, the mixtures were applied in a designated amount given in Table 5.

The phytotoxicity against the wheat was examined 3 weeks after the application. The results are shown in Table 5.

TABLE 5

| Test compound | Amount of active ingredient (g/ha) | Phytotoxicity (%) |
|---|---|---|
| imazosulfuron + Compound [I] | 100 + 100 | 0 |
|  | 100 + 200 | 0 |
|  | 200 + 100 | 0 |
|  | 200 + 200 | 0 |

As shown in the test examples above, the present composition provided excellent herbicidal effect against weeds (e.g., cleavers, wild mustard), and caused no damage against wheat.

INDUSTRIAL APPLICABILITY

According to the present invention, herbicides can be applied in a low dosage for controlling a wide variety of weeds in crop fields or paddy fields.

The invention claimed is:

1. A herbicidal composition which comprises 1-(2-chloroimidazo[1,2-a]pyridine-3-ylsulfonyl)-3-(4,6-dimethoxypyrimidin-2-yl)urea (imazosulfuron) and a compound represented by the formula (I):

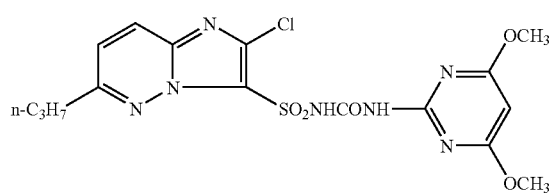

(I)

(Compound [I]) as active ingredients, wherein the weight ration of imazosulfuron: Compound[I] is 1:0.5-1:10.

2. A method for controlling weeds which comprises applying 1-(2-chloroimidazo[1,2-a]pyridine-3-ylsulfonyl)-3-(4,6-dimethoxypyrimidin-2-yl)urea (imazosulfuron) and a compound represented by the formula (I):

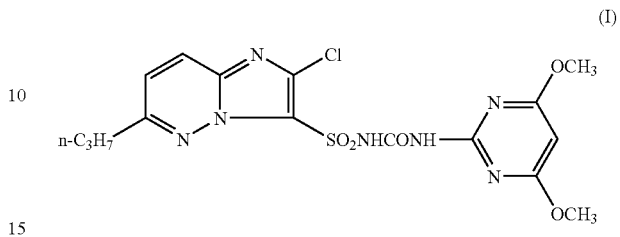

(I)

(Compound [I]) jointly or simultaneously to weeds or soil in a place where the weeds grow or will grow, wherein the weight ration of imazosulfuron: Compound[I] is 1:0.5-1:10.

3. The method for controlling weeds according to claim 2, wherein the weeds are in a wheat field.

4. The method for controlling weeds according to claim 2, wherein the weeds are in a paddy field.

* * * * *